United States Patent [19]
Yoshioka

[11] Patent Number: 5,274,759
[45] Date of Patent: Dec. 28, 1993

[54] ULTRASONIC DIAGNOSTIC APPARATUS CAPABLE OF MULTI-FRAME REPRESENTATION

[75] Inventor: Yoshihisa Yoshioka, Tochigi, Japan

[73] Assignee: Kabushiki Kaisha Toshiba, Kanagawa, Japan

[21] Appl. No.: 885,256

[22] Filed: May 20, 1992

Related U.S. Application Data

[63] Continuation of Ser. No. 549,313, Jul. 9, 1990, abandoned.

[30] Foreign Application Priority Data

Jul. 11, 1989 [JP] Japan .................................. 1-177135

[51] Int. Cl.$^5$ ........................ G06F 15/00; A61B 10/00
[52] U.S. Cl. ............................ 128/660.04; 395/155; 395/139; 395/161
[58] Field of Search ............... 364/413.13, 413.14, 364/413.15, 413.16, 413.17, 413.18, 413.19; 128/660, 661; 395/124, 125, 155, , 161, 139

[56] References Cited

U.S. PATENT DOCUMENTS

| | | | |
|---|---|---|---|
| 4,398,540 | 8/1983 | Takemura et al. | 128/660 |
| 4,423,737 | 1/1984 | Yano et al. | 128/661 |
| 4,608,598 | 8/1986 | Murakami et al. | 358/113 |
| 4,722,345 | 2/1988 | Ueno et al. | 128/660 |
| 5,046,027 | 9/1991 | Taaffe et al. | 364/521 |

Primary Examiner—Phu K. Nguyen
Attorney, Agent, or Firm—Finnegan, Henderson, Farabow, Garrett & Dunner

[57] ABSTRACT

An ultrasonic diagnostic apparatus and an image display apparatus allowing a user to select multiple images for a multi-image format display while sequentially viewing a plurality of full-screen-sized images. Viewing all of the full-sized images before displaying them in a multi-image format allows the user to benefit from the increased resolution of the images as well as requiring only a single routine to read the image data from memory.

10 Claims, 6 Drawing Sheets

DESIRED TOMOGRAPHIC IMAGE SELECTION

BUFFER MEMORY REGIONS

① ② ③ ④

⇓ MULTI-FRAME PROCESS

FIG.3B

MULTI-FRAME DISPLAY

ULTRASONIC DIAGNOSTIC APPARATUS CAPABLE OF MULTI-FRAME REPRESENTATION

This application is a continuation of U.S. application Ser. No. 07/549,313, filed Jul. 9, 1990, now abandoned.

BACKGROUND OF THE INVENTION

1. Field of the Invention

The present invention generally relates to an image display apparatus capable of simultaneously displaying plural images on the same screen. More specifically, the present invention is directed to a so-called multi-frame type display apparatus and also to an ultrasonic diagnostic apparatus capable of representing a plurality of ultrasonic images in a multi-frame mode.

2. Description of the Related Art

A so-called "multi-frame" type ultrasonic diagnostic apparatus is known in the art, for instance, from U.S. Pat. No. 4,398,540 issued on Aug. 16, 1983 to Takemura et. al. entitled "COMPOUND MODE ULTRASOUND DIAGNOSIS APPARATUS". In this conventional ultrasound diagnosis apparatus, for example, both the B-mode image and M-mode image are concurrently displayed on the same TV screen.

In another conventional multi-frame type ultrasonic diagnostic apparatus, more than two, e.g., four ultrasonic images are simultaneously displayed on the same TV screen. That is, the entire TV screen is subdivided into four screen regions. A first selection is made to a plurality of ultrasonic images which have been stored in the buffer memory. In this case, since the selected ultrasonic images are successively displayed on the first subdivided screen region, an operator must successively watch the ultrasonic images displayed on the small (subdivided) screen region. When the first selection is completed, the first-selected ultrasonic image is temporarily stored in the buffer memory and then read out therefrom for the display purpose with ¼-reduced screen size. Thereafter, a second selection is similarly commenced. Thus, the second-selected ultrasonic image is also temporarily stored in this buffer memory and then displayed with another ¼-reduced screen size. After the fourth selection has been accomplished, all these selected ultrasonic images are being simultaneously displayed on the same TV screen with ¼-reduced sizes.

In the above-described conventional multi-frame type image display apparatus, there are the following drawbacks. That is to say, first, the cumbersome image selecting operation is necessarily required in accordance with an increase of the selecting image quantity. Secondly, since such an image selection must be carried out on the small-sized TV screen region, the resolution of one image displayed on such a small-sized TV screen region is not so good as compared with that displayed on the full-sized screen.

As a result, a lengthy selecting operation and a heavy workload are required so as to achieve such a multi-frame image representation. Moreover, the diagnostic capabilities cannot be improved, because the resolution of the multi-frame mode images is not so high.

The present invention has been made in an attempt to solve the above-described drawbacks of the conventional multi-frame type image display apparatus, and therefore has an object to provide a multi-frame type image displaying apparatus and also an ultrasonic diagnostic apparatus utilizing such a multi-frame image display mode, capable of realizing an easy and simple image selecting operation, and also higher resolution of selected images.

SUMMARY OF THE INVENTION

The above-described object and other features of the present invention may be achieved by providing an image display apparatus comprising:

first memory means (5) for sequentially storing a plurality of image data of an object;

multi-frame buffer memory means (8) for temporarily storing said plurality of image data image selecting means for selecting a plurality of selected image data desired by a user from said plurality of image data;

multi-frame image producing means (6) for sequentially storing said plurality of image data from said multi-frame buffer memory means (8), and for producing multi-frame image data constructed of said plurality of selected image data from the multi-frame buffer memory means (8); and display means (7) having a display screen, for selectively displaying one of a plurality of images of the object with a full-screen size in response to said plurality of image data read out from the multi-frame image producing means (6), and also a multi-frame image of the object with a reduced-screen size corresponding to each of the selected image data;

the image selecting means (9:10) being used to select said plurality of selected image data while a plurality of images of the object in full-screen size are sequentially displayed on the display screen of the display means (7) from the multi-frame image producing means (6), said plurality of selected image data being prepared by multi-frame producing means for display on said display screen as a multi-frame image representation purpose.

Furthermore, according to the present invention, an ultrasonic diagnostic apparatus comprises:

ultrasonic image data acquiring means (2:3) for acquiring ultrasonic image data of an object under examination to produce ultrasonic tomographic image data;

first memory means (5) for sequentially storing a plurality of ultrasonic tomographic image data;

multi-frame buffer memory means (8) for temporarily storing said plurality of ultrasonic tomographic image data tomographic image selecting means for selecting a plurality of selected tomographic image data desired by a user from said plurality of ultrasonic image data;

multi-frame image producing means (6) for sequentially storing said plurality of ultrasonic tomographic image data read out from said multi-frame buffer memory means (8), and for producing multi-frame tomographic image data constructed of said plurality of selected tomographic image data retrieved from the multi-frame buffer memory means (8);

display means (7) having a display screen, for selectively displaying one of a plurality of ultrasonic tomographic image of the object under examination with a full-screen size in response to said plurality of ultrasonic tomographic image data out from the multi-frame image producing means (6), and a multi-frame ultrasonic tomographic image of the object with a reduced-screen size corresponding to each of the selected tomographic image data, The tomographic image selecting means (9:10) being used to select said plurality of selected tomographic image data while a plurality of tomographic images of the object with the full-screen size are sequentially displayed on the display screen of the display means from the multi-frame image producing means (6), said plurality of selected tomographic image data being prepared by a multi-frame image producing means for display on said display means as a multi-frame tomographic representation.

BRIEF DESCRIPTION OF THE DRAWINGS

The present invention will be more readily understood on reading the following description with reference to the accompanying drawings, in which.

DETAILED DESCRIPTION OF THE PREFERRED EMBODIMENTS

OVERALL ARRANGEMENT OF MULTI-FRAME TYPE ULTRASONIC DIAGNOSTIC APPARATUS

Figure 1:
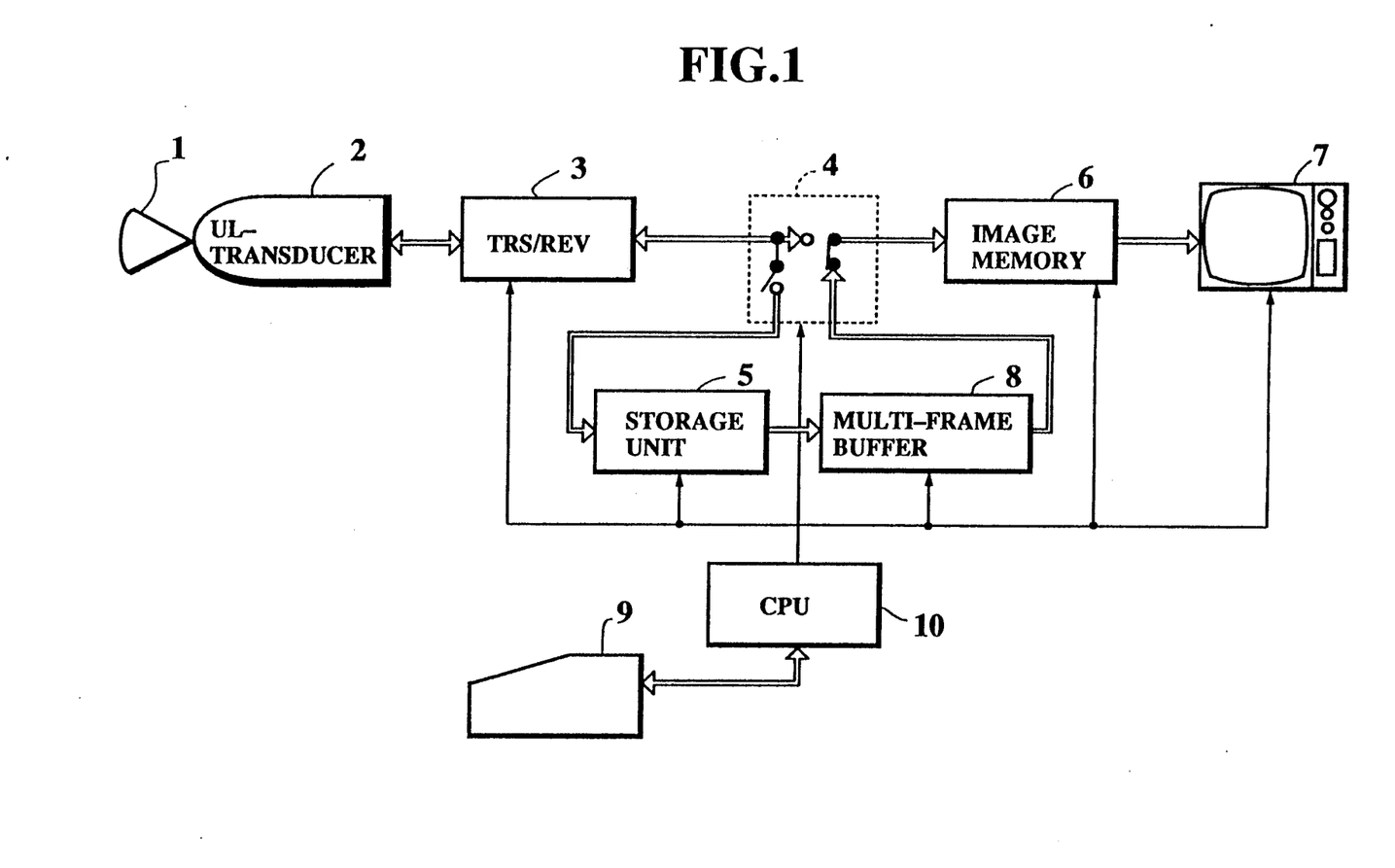
FIG. 1 is a schematic block diagram of a multi-frame type ultrasonic diagnostic apparatus according to a first preferred embodiment of the present invention.

In FIG. 1, there is shown an overall arrangement of a multi-frame type ultrasonic diagnostic apparatus according to a first preferred embodiment of the present invention.

In the first multi-frame type ultrasonic diagnostic apparatus shown in FIG. 1, ultrasonic waves 1 are transmitted from an ultrasonic transducer 2 to an biological body (not shown) under medical examination under the control of a transmitter/receiver circuit 3, and ultrasonic echoes reflected from the biological body are received by this transducer 2 to produce reception echo signals. These echo signals are processed in the transmitter/receiver circuit 3 so as to sequentially produce ultrasonic tomographic images for each TV (television) frame. A mode changing switch 4 is employed to receive the ultrasonic tomographic image data from the transmitter/receiver circuit 3, and simultaneously supply the tomographic image data to a storage unit 5 for the multi-frame mode, and also to an image memory unit 6 for the real-time imaging mode.

On the other hand, the output of the storage unit 5 having the large memory capacity is connected to a multi-frame buffer memory circuit 8 whose output is connected via the mode changing switch 4 to an image memory unit 6. The function of this image memory 6 unit is first to sequentially store therein the tomographic image data and secondly to produce the multi-frame image which will be displayed on the display unit 7 with reduced screen sizes. A central processing unit (referred to as a "CPU") 10 is employed so as to control the above-described transmitter/receiver circuit 3, mode changing switch 4, storage unit 5, image memory unit 6, multi-frame buffer memory circuit 8, and display unit 7.

OVERALL OPERATION

In the real-time image display mode, the ultrasonic tomographic image data are supplied as follows. That is to say, when the ultrasonic images are displayed and observed on the display unit 7 in the real-time mode, the ultrasonic image data derived from the transmitter/receiver circuit 3 are directly supplied via the mode changing switch 4 to the image memory unit 6 and simultaneously to the storage unit 5, so that a plurality of tomographic image data are sequentially written into this storage unit 5 and also sequentially read out from the image memory 6 for real-time displays.

In this real-time display mode, each of these tomographic images is successively displayed on the display unit 7 with a full-screen size, namely displayed on the overall display screen.

Then, in the multi-frame display mode, the ultrasonic diagnostic apparatus shown in FIG. 1 is operated as follows.

Figure 2:
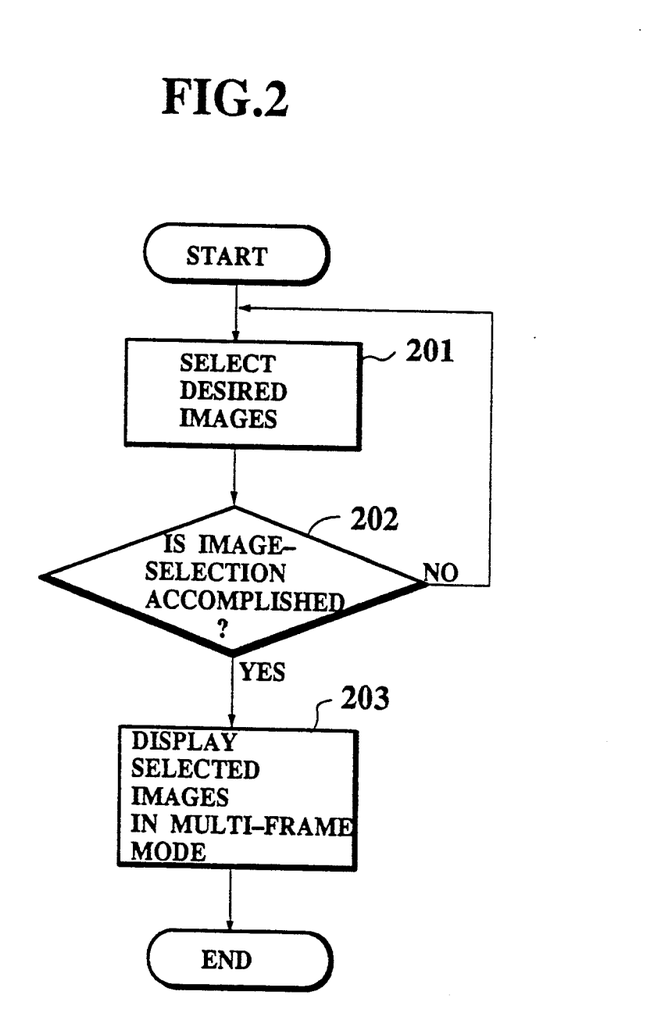
FIG. 2 is a flowchart for briefly explaining an overall operation of the multi-frame type ultrasonic diagnostic apparatus shown in FIG. 1.
Figure 3A:
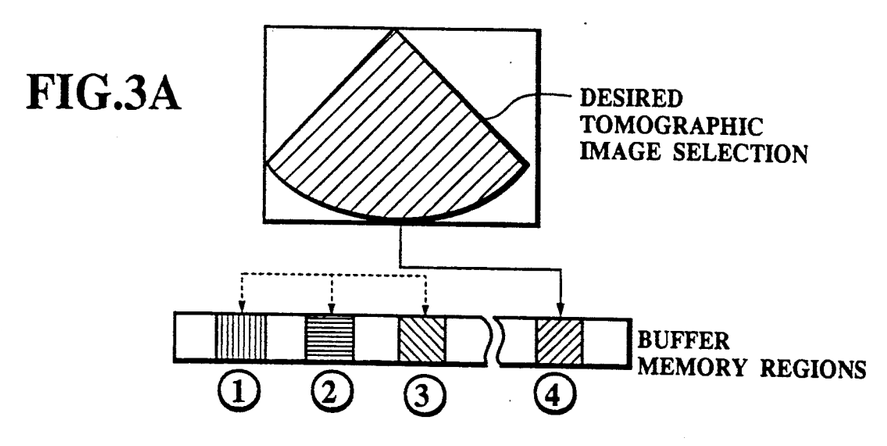
FIGS. 3A and 3B are illustrations for explaining the desired image selection and multi-frame display operation performed in the apparatus shown in FIG. 1.
Figure 3B:
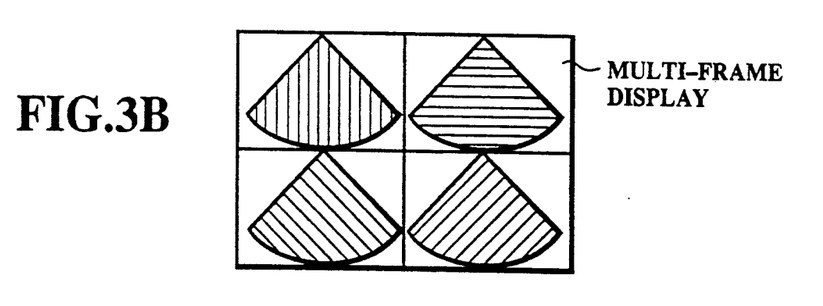

This multi-frame display mode will now be described with reference to a flowchart shown in FIG. 2 and an explanatory operation shown in FIG. 3.

Assuming now that a plurality of ultrasonic tomographic images are sequentially displayed one by one in a full-screen size on the display unit 7. A selection is made of, for example, four desired tomographic images which should be later displayed on the corresponding ¼-reduced screen regions of the display unit 7 by operating the keyboard 9 at a step 201 of the flowchart shown in FIG. 2. When the image selection is accomplished at a next step 202, the process is advanced to a step 203 in which the selected four images are displayed in the multi-frame mode. In other words, when four desired tomographic images have been separately selected at the step 202 with being displayed in a full-screen sized image, all of these four images are simultaneously displayed on the same screen of the display unit 7 in the ¼-reduced screen size for each image (see the illustration of FIG. 3A).

To the contrary, when such an image selection is not yet completed at the step 202, then the process is returned to the previous step 201 in which a further image selection is made.

Precisely speaking, when the desired image selection has been completed at the step 202, the selected tomographic image data are sequentially and temporarily written from the storage unit 5 into the multi-frame buffer memory circuit 8 in a designated order by an automatic operation mode or by manipulating the keyboard 9. Subsequently, a multi-frame display image is electronically constructed in the image memory circuit 6, as previously stated. Accordingly, the multi-frame display image constructed of the selected four tomographic images can be displayed as represented in the display condition of FIG. 3B.

DETAILED CIRCUIT ARRANGEMENT OF MULTI-FRAME TYPE ULTRASONIC DIAGNOSTIC APPARATUS

Figure 4:
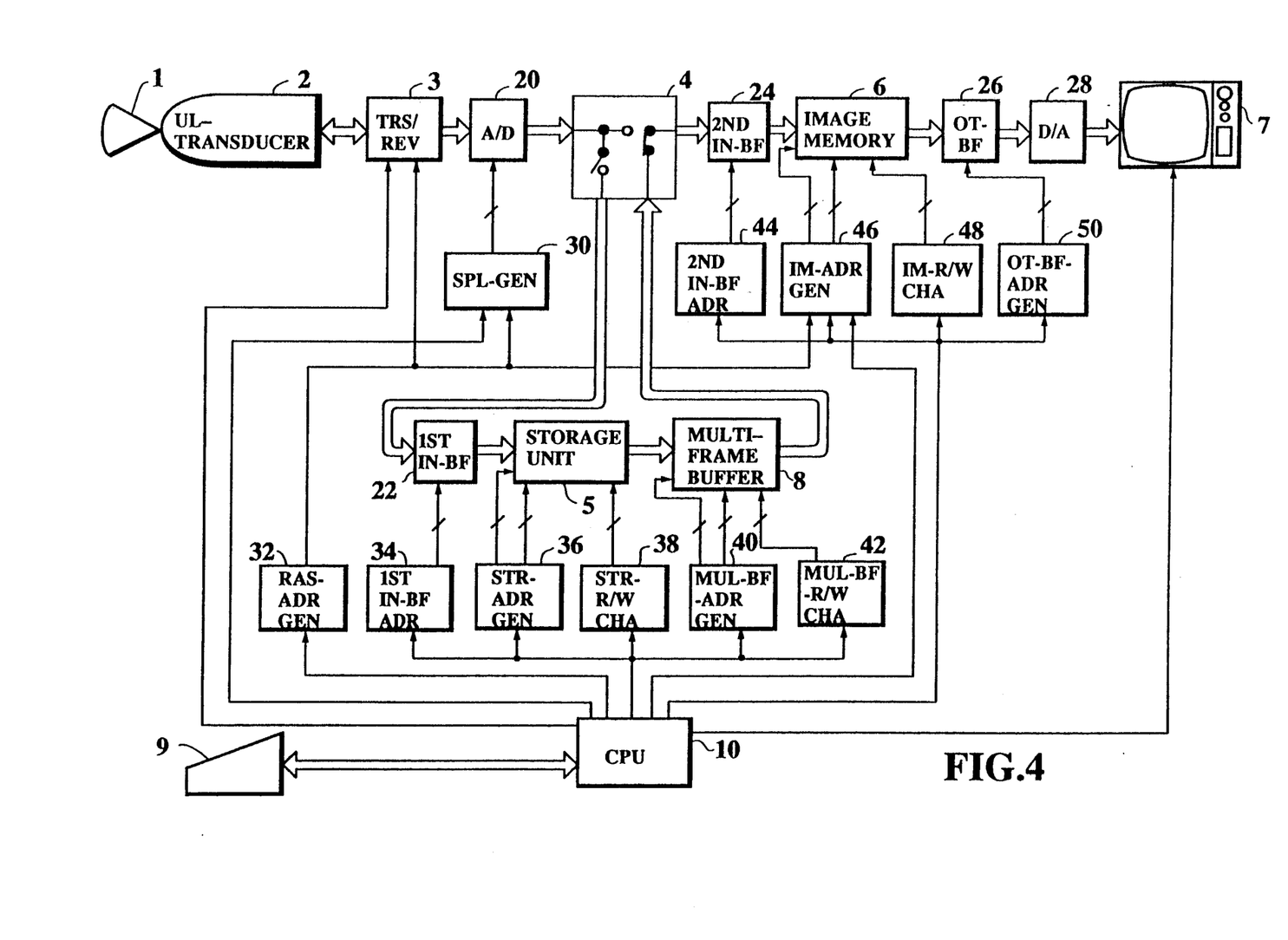
FIG. 4 is a schematic block diagram for representing a detailed circuit arrangement of the ultrasonic diagnostic apparatus shown in FIG. 1; and, FIG. 5 and 6 are flowcharts for explaining the multi-frame display operation of the multi-frame buffer memory circuit employed in the apparatus shown in FIG. 4.

In FIG. 4, there is shown a detailed circuit arrangement of the multi-frame type ultrasonic diagnostic apparatus according to the first preferred embodiment.

As apparent from FIG. 4, the ultrasonic echo signals produced in the transmitter/receiver circuit 3 are analog-to-digital-converted into ultrasonic echo data by an A/D converter 20. The ultrasonic echo data are supplied via the mode changing switch 4 to a first input buffer 22 and thereafter supplied to the storage unit 5. In the multi-frame image display mode, these ultrasonic echo data are temporarily stored in the multi-frame buffer memory circuit 8, which will be read out and furnished via the mode changing switch 4 and also a second input buffer 24 to the image memory unit 6. Subsequently, the echo data are read out from this image memory unit 6 and supplied via an output buffer 26 and a digital-to-analog converter 28 to the display unit 7. That is, the echo data read out from the image memory unit 6 are temporarily stored in the output buffer 26 and then are digital-to-analog-converted into corresponding ultrasonic tomographic image signal by the D/A converter 28.

To achieve the above-described operations of the multi-frame type ultrasonic diagnostic apparatus, there are further provided various control circuits. That is, the A/D converter 20 is under control of a sampling pulse generator 30 which is also controlled via a raster address generator 32 by the CPU 10. The first input buffer 22 is under control of a first input buffer address generator 34. The storage unit 5 is controlled by a storage unit address generator 36 and a storage unit read/write changer 38. On the other hand, the multi-frame buffer memory circuit 8 is controlled by a multi-frame buffer memory generator 40 and a multi-frame buffer read/write changer 42. The second input buffer 24 is under control of a second input buffer address generator 44. The image memory unit 6 is controlled by an image memory address generator 46 and an image memory read/write charger 48. The output buffer 26 is under control of an output buffer address generator 50. As is known in the art, the CPU 10 controls all these control circuits, address generators and changers.

DETAILED OPERATION OF MULTI-FRAME BUFFER MEMORY CIRCUIT

Referring now to flowcharts shown in FIGS. 5 and 6, the multi-frame buffering operation, a major feature of the present invention, will be described more in detail.

Figure 5:
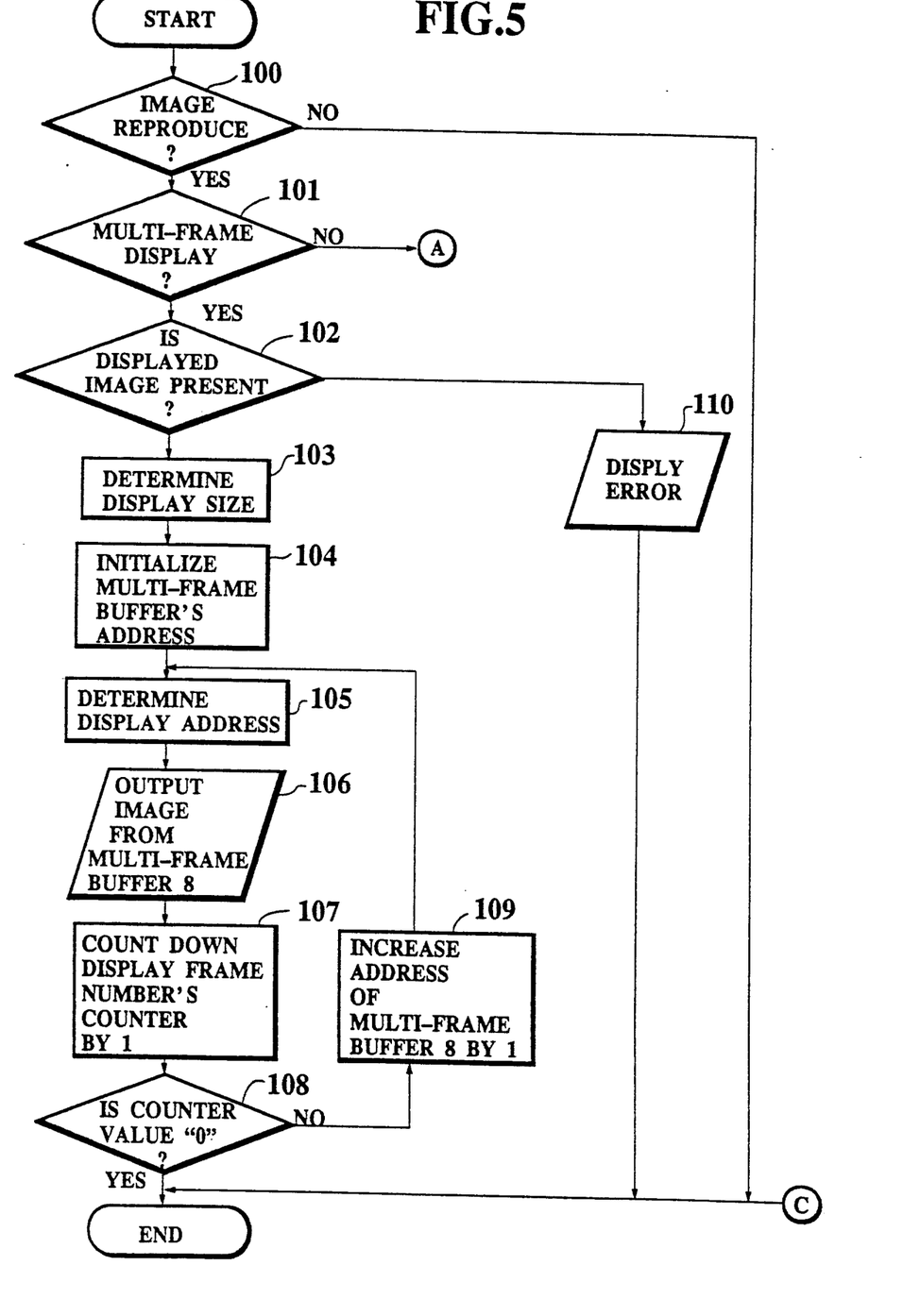

In the flowchart shown in FIG. 5, a first check is made whether or not an image is required to be reproduced at a step 100. In this case, since a check result is YES, then another judgement is made whether or not a multi-frame image is displayed at a step 101. If YES, then the operation is advanced to a step 102. At this step 102, a further check is made whether or not the image is present. If NO, then an "error" message is displayed on the display unit 7 at a step 110 and thereafter the process is ended.

To the contrary, if YES, then a display size in accordance with the displayed frame (image) number at a step 103. Subsequently, an address of the multi-frame buffer memory circuit 8 is initialized at a step 104 and a display address of the display unit 7 is determined at a step 105. As a result, the selected tomographic image data is outputted from the multi-frame buffer memory circuit 8 at a step 106. Then, a counter (not shown in detail) for the displayed frame number is counted down by 1. A judgement is made whether or not the count value is equal to "0" at a step 108. If YES, then this process is completed. If NO, the address of the multi-frame buffer memory circuit 8 is increased by 1, which is performed by operating the multi-frame buffer address generator 40 shown in FIG. 4 under the control of the CPU 10.

Figure 6:
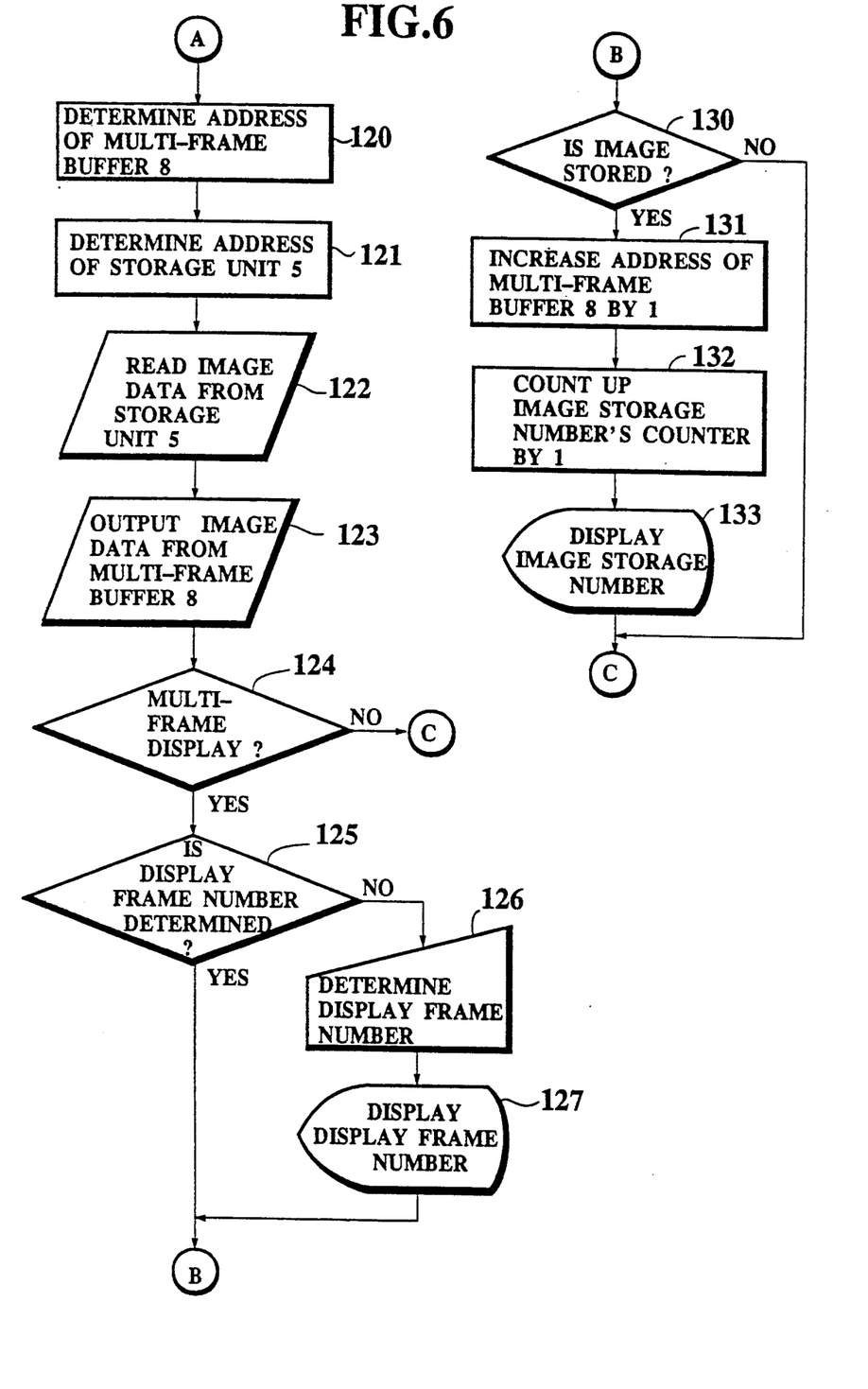

Returning to the previous step 101, if the judgement result is "NO", then the process is advanced to a step 120 represented in FIG. 6A. At this step 120, the address of the multi-frame buffer memory circuit 8 is determined. Thereafter, another address of the storage unit 5 is determined at a step 121 so as to read out the selected tomographic image data from this storage unit 5 at a step 122, and then the image data is outputted from the multi-frame buffer memory circuit 8 at a step 123.

At a subsequent step 124, a judgement is made whether or not the multi-frame display is required. If NO, then this process is accomplished. To the contrary, if YES, then another judgement is made whether or not the display frame number is determined at a step 125. If NO, then this display frame number is determined at a step 126, and also the multi-frame number is displayed on the display unit 7 at a step 127. Thereafter the process is advanced to a next step 130 as shown in FIG. 6B. Similarly, if the judgement result becomes YES at the previous step 125, then the process is advanced to this check step 130.

At the step 130, a check is made whether or not displayed image (frame) is required to be stored. If YES, then the process is proceeded to a step 131 in which the address of the multi-frame buffer memory circuit 8 is increased by 1. At a next step 132, a counter (not shown in detail) for the image storage number is counted up by 1. As a consequence, this image storage number is displayed at a step 133. Then, if the judgement result becomes NO at the previous step 130, this process is ended.

MODIFICATIONS

As apparent from the foregoing descriptions, the present invention is not limited to the above-described ultrasonic diagnostic apparatus, but may be modified without departing from the technical scope of the present invention.

For instance, the multi-frame display idea of the present invention was embodied in the multi-frame type ultrasonic diagnostic apparatus in the first preferred embodiment. This display idea may be realized as a multi-frame type image display apparatus.

Moreover, although four frames were simultaneously displayed on the same screen of the display unit 7 in the first preferred embodiment, other frame numbers may be, of course, utilized.

As previously described in detail, in accordance with the present invention, since the image selection for the multi-frame display purpose is done while observing the images displayed with the full-screen size, the desired images can be selected with maintaining the better image quality for the diagnostic purpose. Moreover, since there is required only one routine to read out the selected desirable image data from the multi-frame buffer memory circuit 8, such a desirable image selection can be achieved at higher efficiency, as compared with the conventional image selection.

What is claimed is:

1. An image display apparatus comprising:
   first memory means for sequentially storing a plurality of image data of an object;
   multi-frame buffer memory means for temporarily storing said plurality of image data;
   image selecting means for selecting a plurality of selected image data desired by a user from said plurality of image data;
   multi-frame image producing means for sequentially storing said plurality of image data from said multi-frame buffer memory means, and for producing multi-frame image data constructed of said plurality of selected image data from the multi-frame buffer memory means; and display means having a display screen for selectively displaying one of a plurality of images of the object with a full-screen size in response to said plurality of image data from the multi-frame image producing means, and a multi-frame image of the object with a reduced-screen size corresponding to each of the selected image data;

the image selecting means being used to select said plurality of selected image data while a plurality of images of said object in full-screen size are sequentially displayed on said display screen.

2. An image display apparatus as claimed in claim 1, wherein a total number of said selected image data is selected to be 4, whereby said multi-frame image of the object is constructed of 4 selected images, each of which is displayed with a ¼-reduced screen size of the screen.

3. An image display apparatus as claimed in claim 1, wherein a memory capacity of said first memory means is larger than that of said multi-frame image producing means.

4. An ultrasonic diagnostic apparatus comprising:

ultrasonic image data acquiring means for acquiring ultrasonic image data of an object to produce ultrasonic tomographic image data;

first memory means for sequentially storing a plurality of ultrasonic tomographic image data;

multi-frame buffer memory means for temporarily storing said plurality of ultrasonic tomographic image data;

tomographic image selecting means for selecting a plurality of selected tomographic image data desired by a user from said plurality of ultrasonic image data;

multi-frame image producing means for sequentially storing said plurality of ultrasonic tomographic image data from said multi-frame buffer memory means, and for producing multi-frame tomographic image data constructed of said plurality of selected tomographic image data from the multi-frame buffer memory means; and display means having a display screen for selectively displaying one of a plurality of ultrasonic tomographic images of said object with a full-screen size in response to said plurality of ultrasonic tomographic image data from the multi-frame image producing means, and a multi-frame ultrasonic tomographic image of the object with a reduced-screen size corresponding to each of the selected tomographic image data;

the tomographic image selecting means being used to select said plurality of selected tomographic image data while a plurality of tomographic images of said object in full-screen size are sequentially displayed on said display screen.

5. An ultrasonic diagnostic apparatus as claimed in claim 4, wherein said ultrasonic image data acquiring means includes:

an ultrasonic transducer for transmitting ultrasonic waves to the object under examination and for receiving ultrasonic echoes reflected from the object to produce ultrasonic echo signals; and, a transmitter/receiver circuit for transmitting an excitation pulse to the ultrasonic transducer so as to produce the ultrasonic waves and for receiving the ultrasonic echo signals thereto to produce the ultrasonic tomographic image data.

6. An ultrasonic diagnostic apparatus as claimed in claim 4, wherein said first memory means includes:

a storage unit for sequentially storing said plurality of ultrasonic tomographic image data;

a storage address generator for generating read/write addresses of the storage unit; and, a storage read/write changing circuit for changing read/write operations of the storage unit by utilizing the read/write addresses.

7. An ultrasonic diagnostic apparatus as claimed in claim 4, wherein said multi-frame buffer memory means includes:

a multi-frame buffer memory circuit having at least a first memory region for temporarily storing said plurality of ultrasonic tomographic image data derived from the first memory means, and also a second memory region for sequentially fetching said plurality of ultrasonic tomographic image data selected by the tomographic image selecting means.

8. An ultrasonic diagnostic apparatus as claimed in claim 7, wherein said multi-frame buffer memory means further includes:

a buffer memory address generator for generating read/write addresses of the multi-frame buffer memory circuit; and, a buffer memory read/write changing circuit for changing read/write operations of both said first and second memory regions by utilizing the read/write addresses.

9. An ultrasonic diagnostic apparatus as claimed in claim 4, wherein a memory capacity of said first memory means is selected to be greater than that of said multi-frame image producing means.

10. An ultrasonic diagnostic apparatus as claimed in claim 4, wherein a total number of said selected tomographic image data is selected to be 4, whereby said multi-frame tomographic image of the object is constructed of 4 selected tomographic images, each of which is displayed with a ¼-reduced screen size of the display screen.

* * * * *